US012725696B2

(12) United States Patent
Lee et al.

(10) Patent No.: US 12,725,696 B2
(45) Date of Patent: Sep. 1, 2026

(54) METHOD FOR RECONSTRUCTING ECG SIGNALS THROUGH IMAGING FOR ARRHYTHMIA DETECTION AND ITS DETECTION SYSTEM

(71) Applicant: National Cheng Kung University, Tainan City (TW)

(72) Inventors: Shuenn-Yuh Lee, Tainan City (TW); Chun-Rong Huang, Tainan City (TW); Ju-Yi Chen, Tainan City (TW); Kai-Ze Lei, Kaohsiung City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 0 days.

(21) Appl. No.: 18/963,386

(22) Filed: Nov. 27, 2024

(65) Prior Publication Data

US 2025/0285739 A1 Sep. 11, 2025

(30) Foreign Application Priority Data

Mar. 6, 2024 (TW) ................................ 113108210

(51) Int. Cl.
*G16H 30/40* (2018.01)
*A61B 5/00* (2006.01)
(Continued)

(52) U.S. Cl.
CPC ........... *G16H 30/40* (2018.01); *A61B 5/0077* (2013.01); *A61B 5/02416* (2013.01);
(Continued)

(58) Field of Classification Search
CPC ...... G16H 30/40; G16H 50/20; A61B 5/0077; A61B 5/02416; A61B 5/0245;
(Continued)

(56) References Cited

U.S. PATENT DOCUMENTS

2015/0366518 A1* 12/2015 Sampson ............. A61B 5/7264 600/509
2019/0239761 A1* 8/2019 Tao ........................... G06T 5/40
(Continued)

FOREIGN PATENT DOCUMENTS

CN 114913986 A * 8/2022 .......... G06F 18/241

*Primary Examiner* — Oommen Jacob
(74) *Attorney, Agent, or Firm* — LANWAY IPR SERVICES; Chun-Ming Shih

(57) ABSTRACT

Method for reconstructing ECG signals through imaging for arrhythmia detection and its detection system, wherein the method for reconstructing ECG signals through imaging for arrhythmia detection involves receiving images of the human skin, which contain color changes on the skin surface caused by heartbeats and heart rhythms. The method comprises performing noise reduction on these color changes and analyzing the color variations to extract a remote photoplethysmographic (rPPG) signal that corresponds to the heart rates and heart rhythms. Frequency domain analysis is conducted to identify the frequency features within the rPPG signal, and feature extraction is performed on these frequency characteristics to obtain a photoplethysmographic (PPG) signal. The PPG signal undergoes feature extraction to derive time domain features and frequency domain features, which are then fused to output a reconstructed ECG signal. Finally, the waveform characteristics of the reconstructed ECG signal are interpreted, allowing for the identification of classifications corresponding to arrhythmias based on these waveform features.

18 Claims, 12 Drawing Sheets

(51) Int. Cl.

| | |
|---|---|
| ***A61B 5/024*** | (2006.01) |
| ***A61B 5/0245*** | (2006.01) |
| ***A61B 5/103*** | (2006.01) |
| ***A61B 5/364*** | (2021.01) |

(52) U.S. Cl.
CPC .......... *A61B 5/0245* (2013.01); *A61B 5/1032* (2013.01); *A61B 5/364* (2021.01)

(58) Field of Classification Search
CPC ..... A61B 5/1032; A61B 5/364; A61B 5/7203; A61B 5/7264; A61B 5/7267
See application file for complete search history.

(56) References Cited

U.S. PATENT DOCUMENTS

| | | | | |
|---|---|---|---|---|
| 2020/0100693 | A1* | 4/2020 | Velo | G16H 50/20 |
| 2021/0202061 | A1* | 7/2021 | Holsti | G06F 3/014 |
| 2022/0280072 | A1* | 9/2022 | Timofejevs | G06F 18/24147 |
| 2023/0000376 | A1* | 1/2023 | Maman | G06N 3/0464 |
| 2025/0082211 | A1* | 3/2025 | Chan | A61B 5/02438 |
| 2025/0285739 | A1* | 9/2025 | Lee | G16H 50/20 |

* cited by examiner

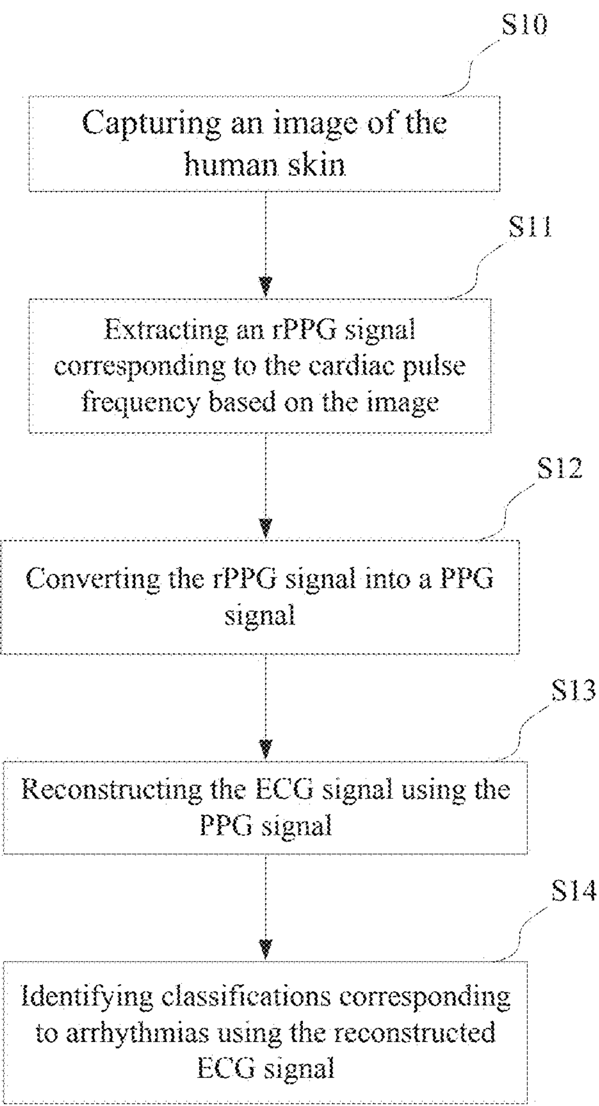
【FIG.1】

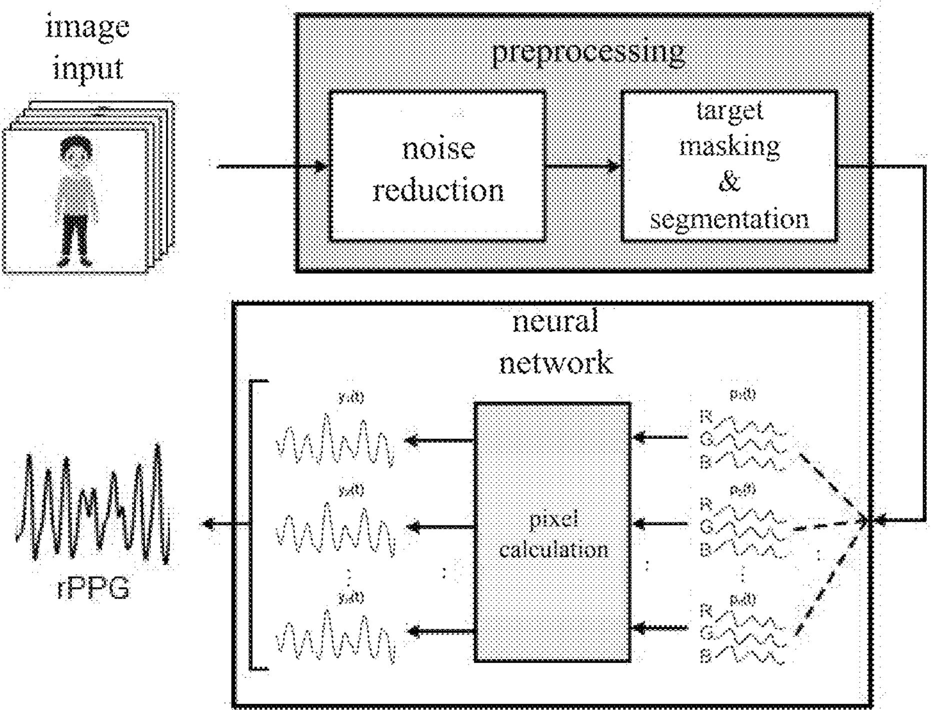
【FIG.2】

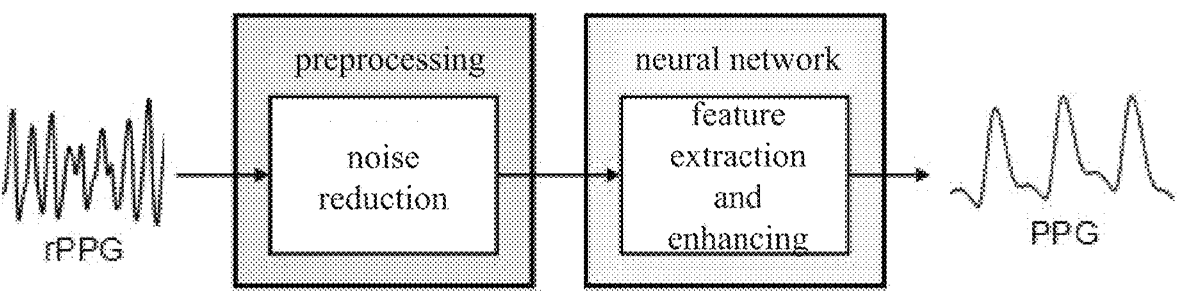
【FIG.3】

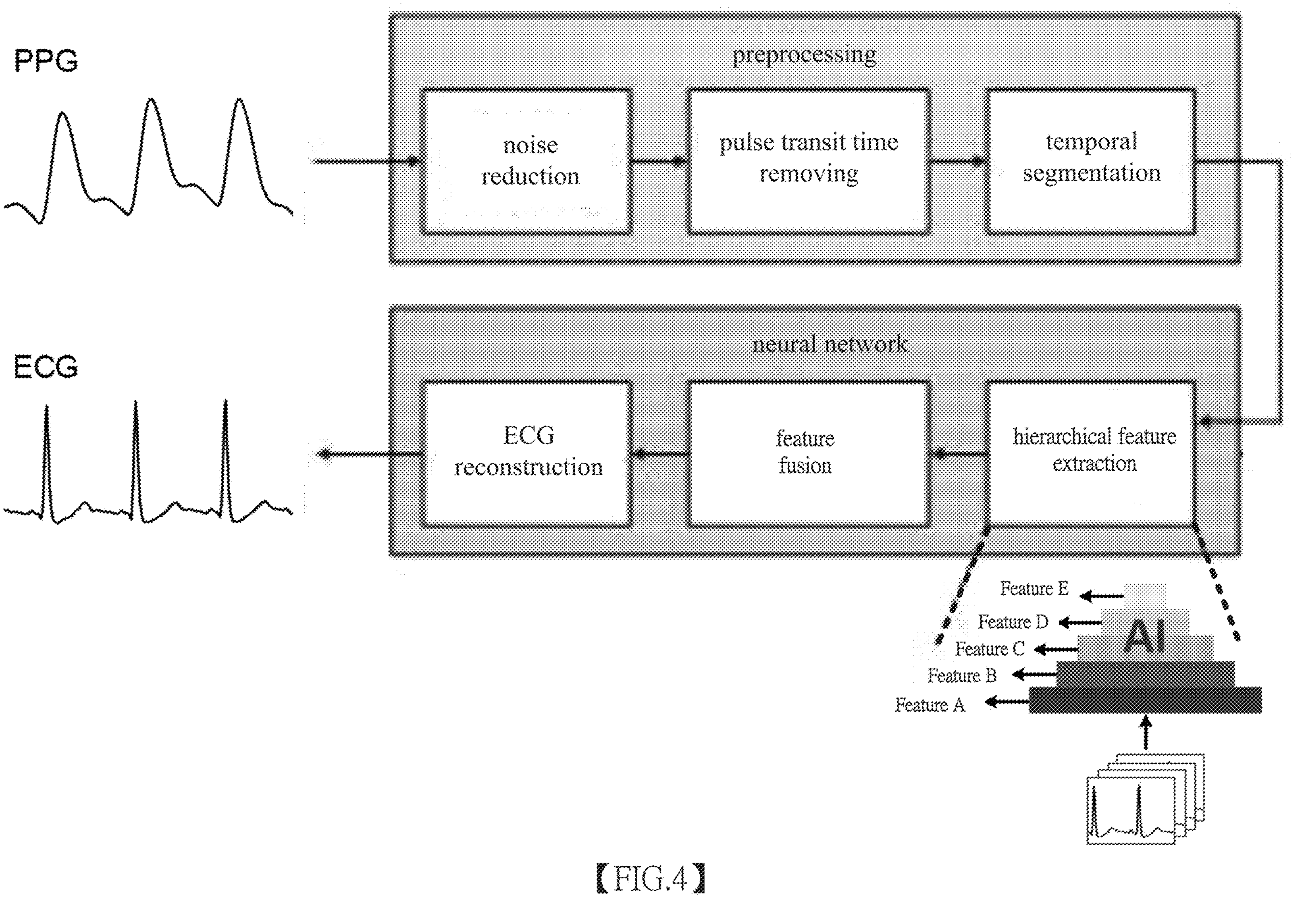
【FIG.4】

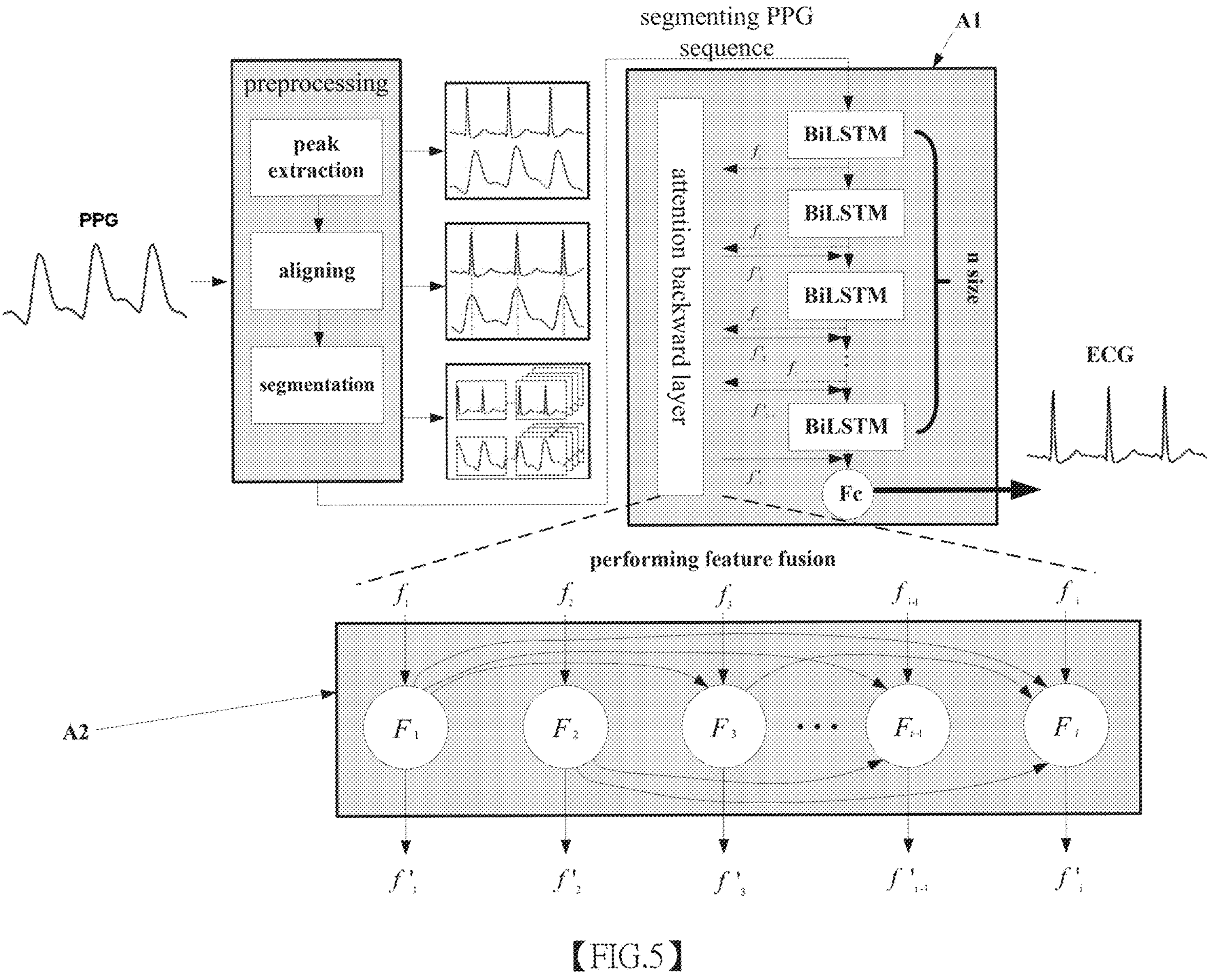
【FIG.5】

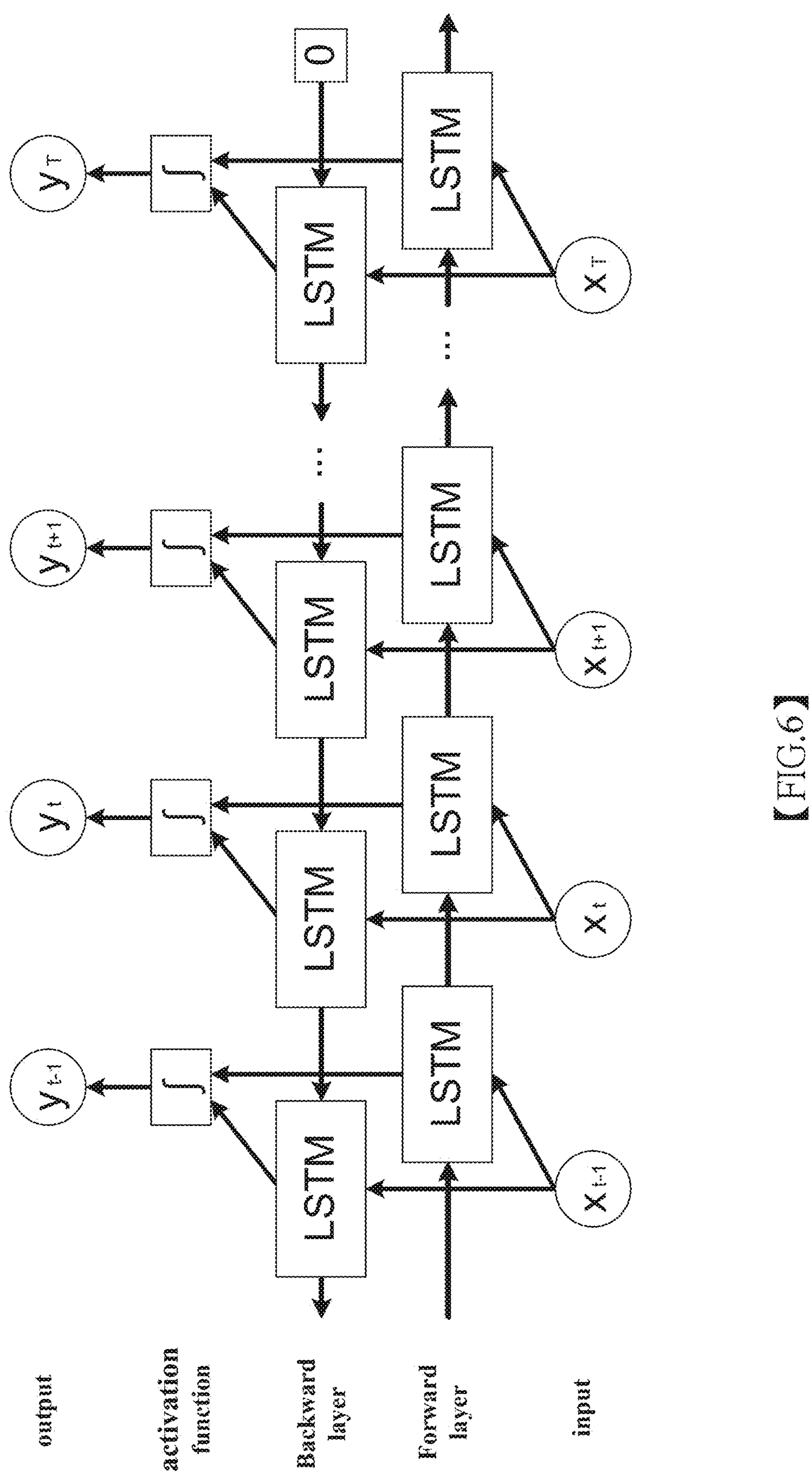
【FIG.6】

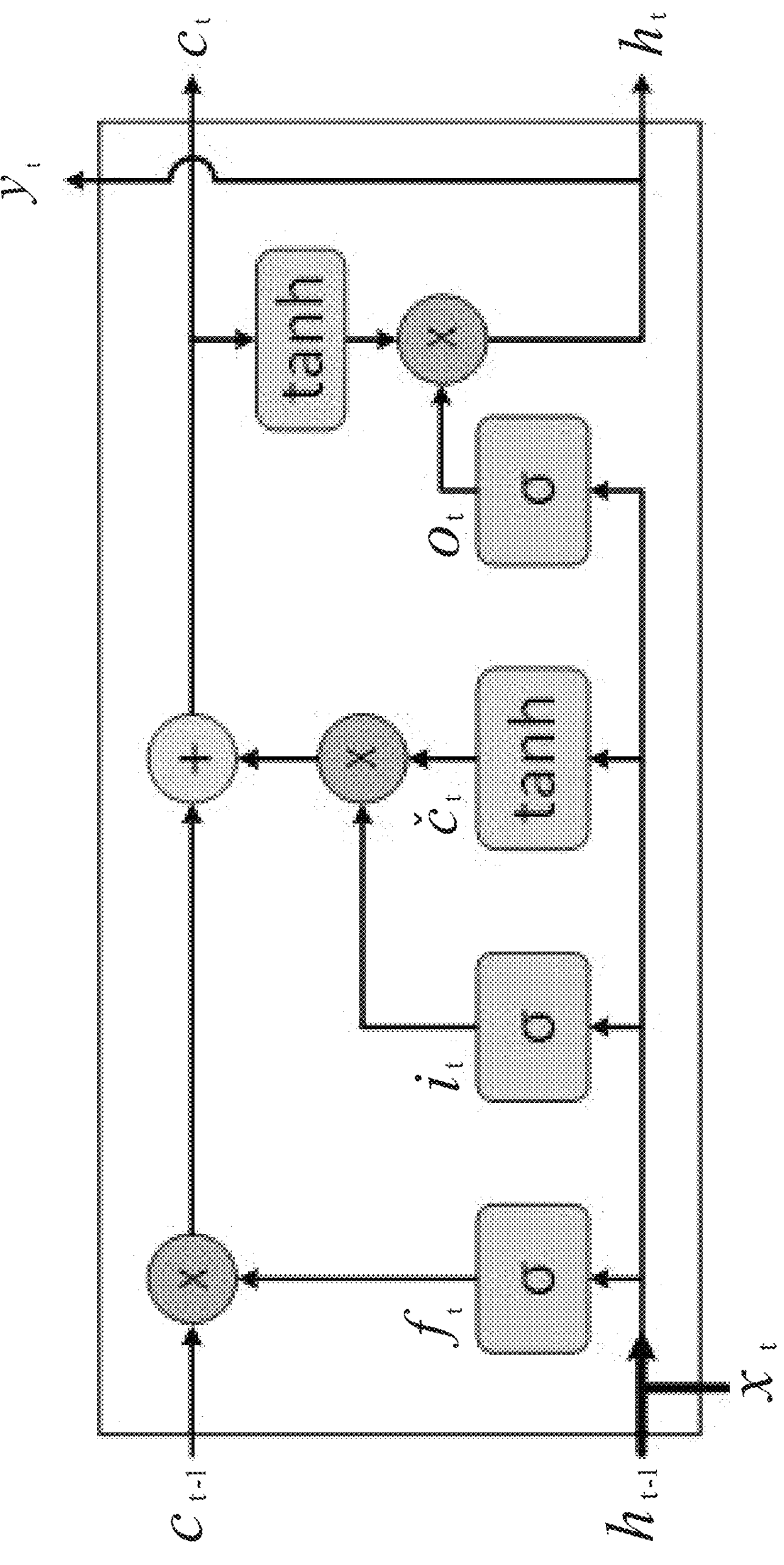
【FIG.7】

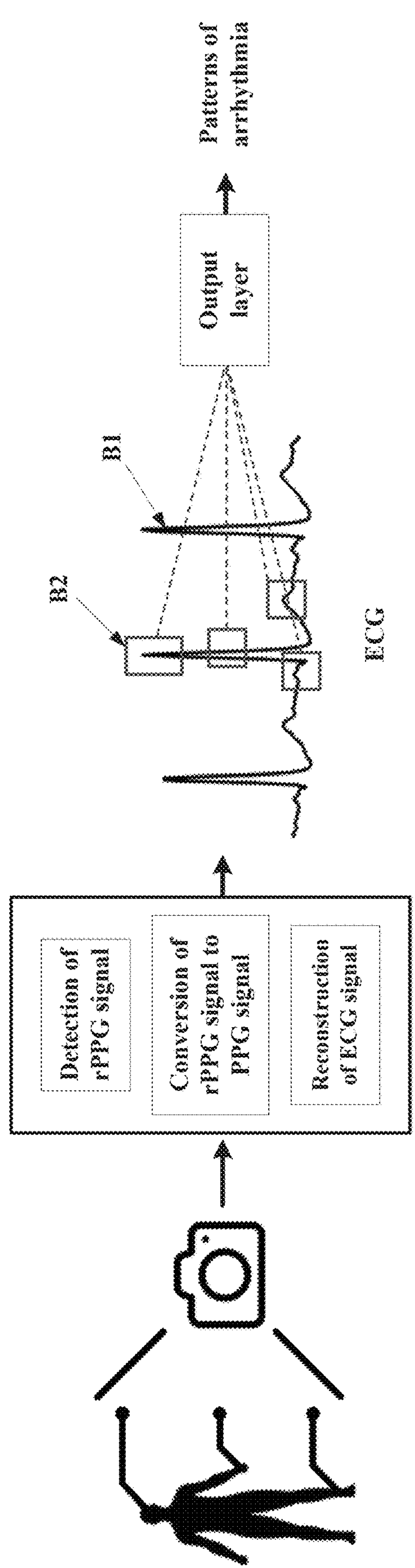
【FIG.8】

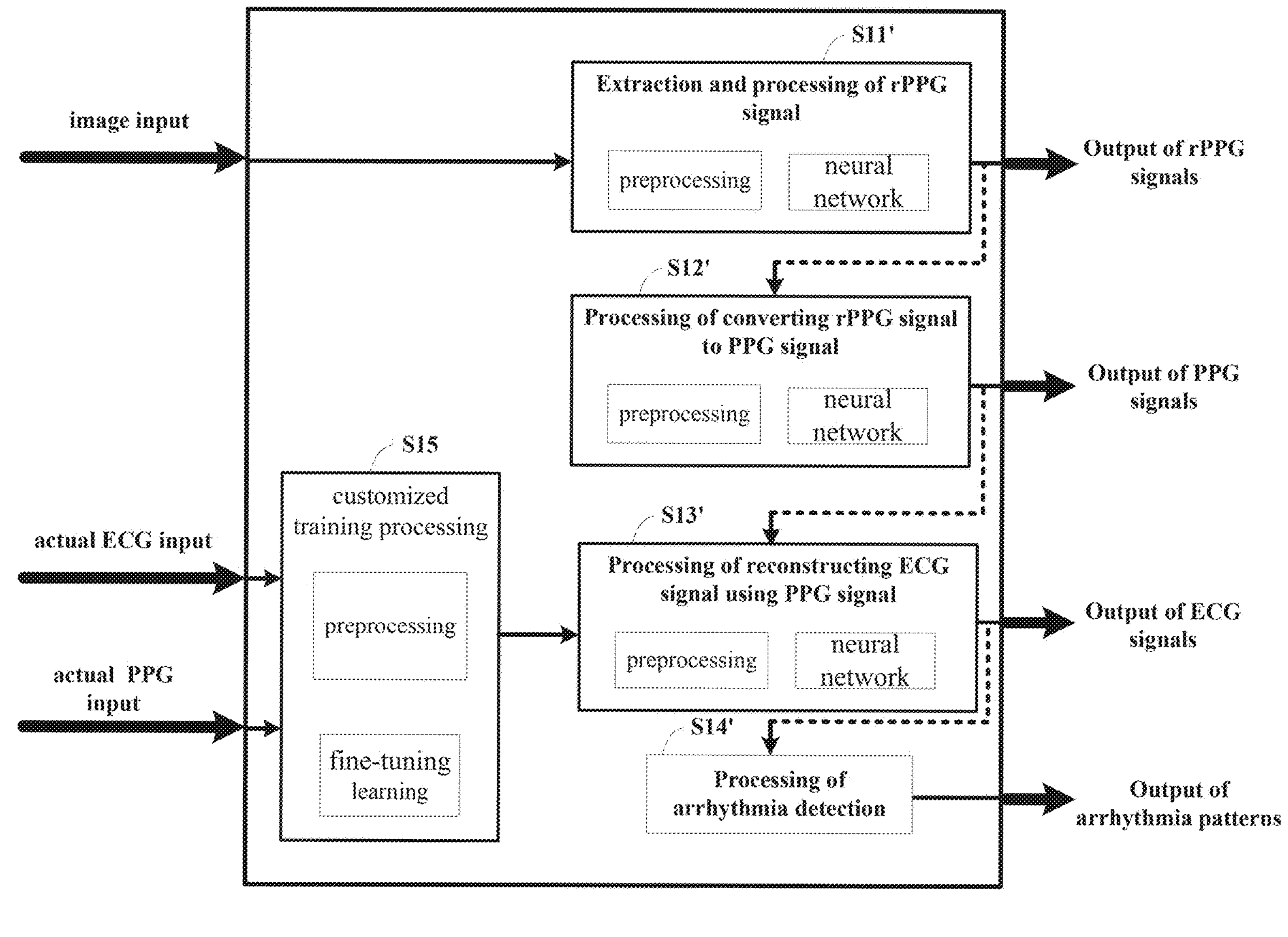
【FIG.9】

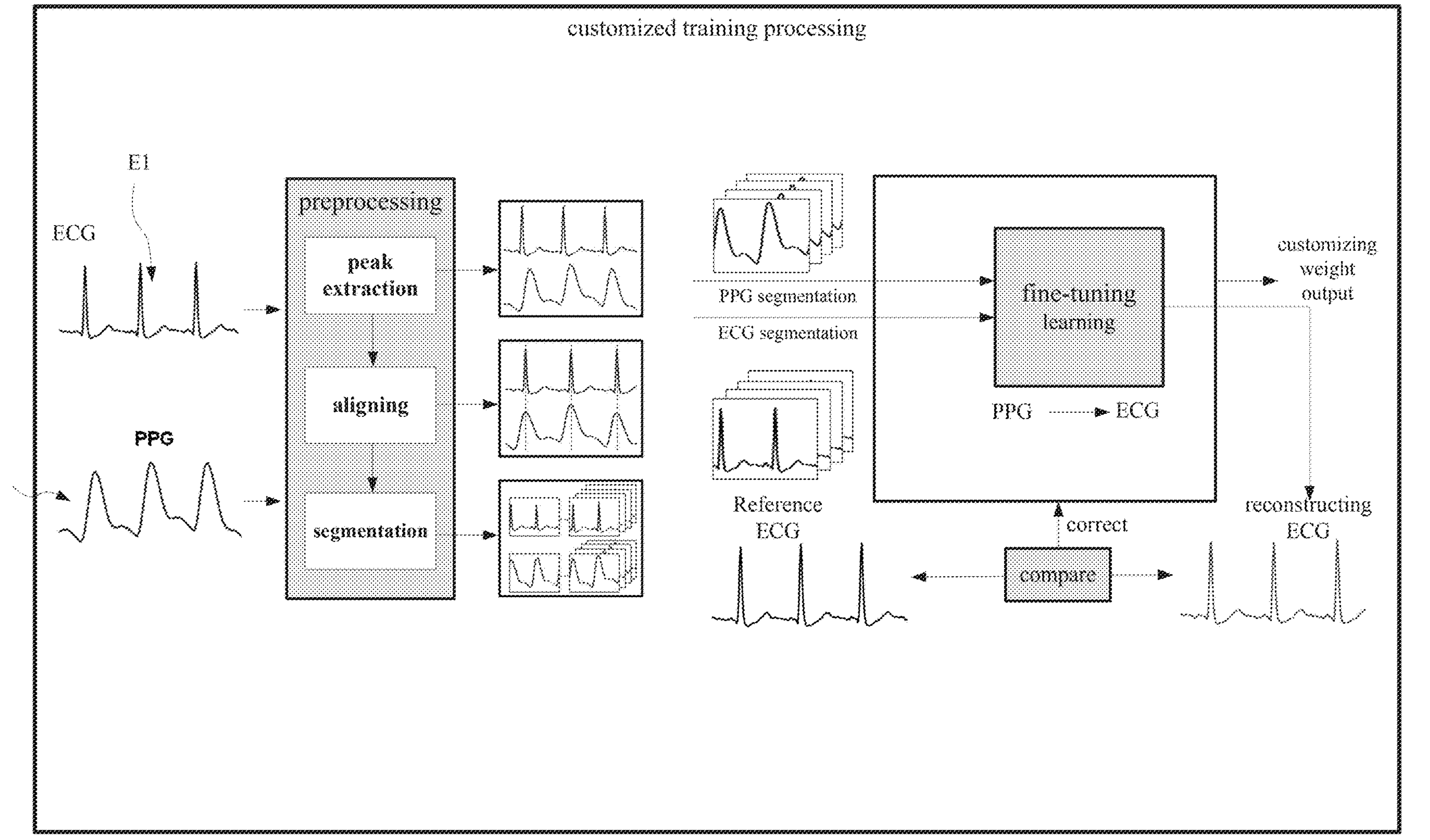
【FIG.10】

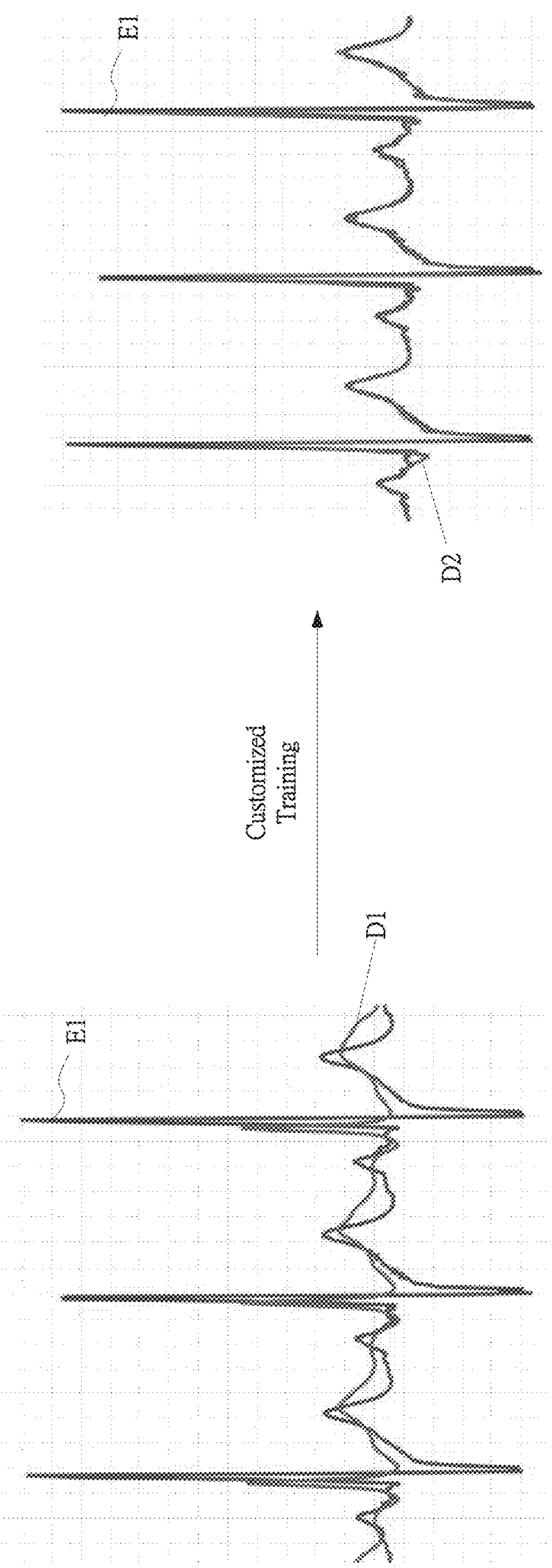
【FIG.11】

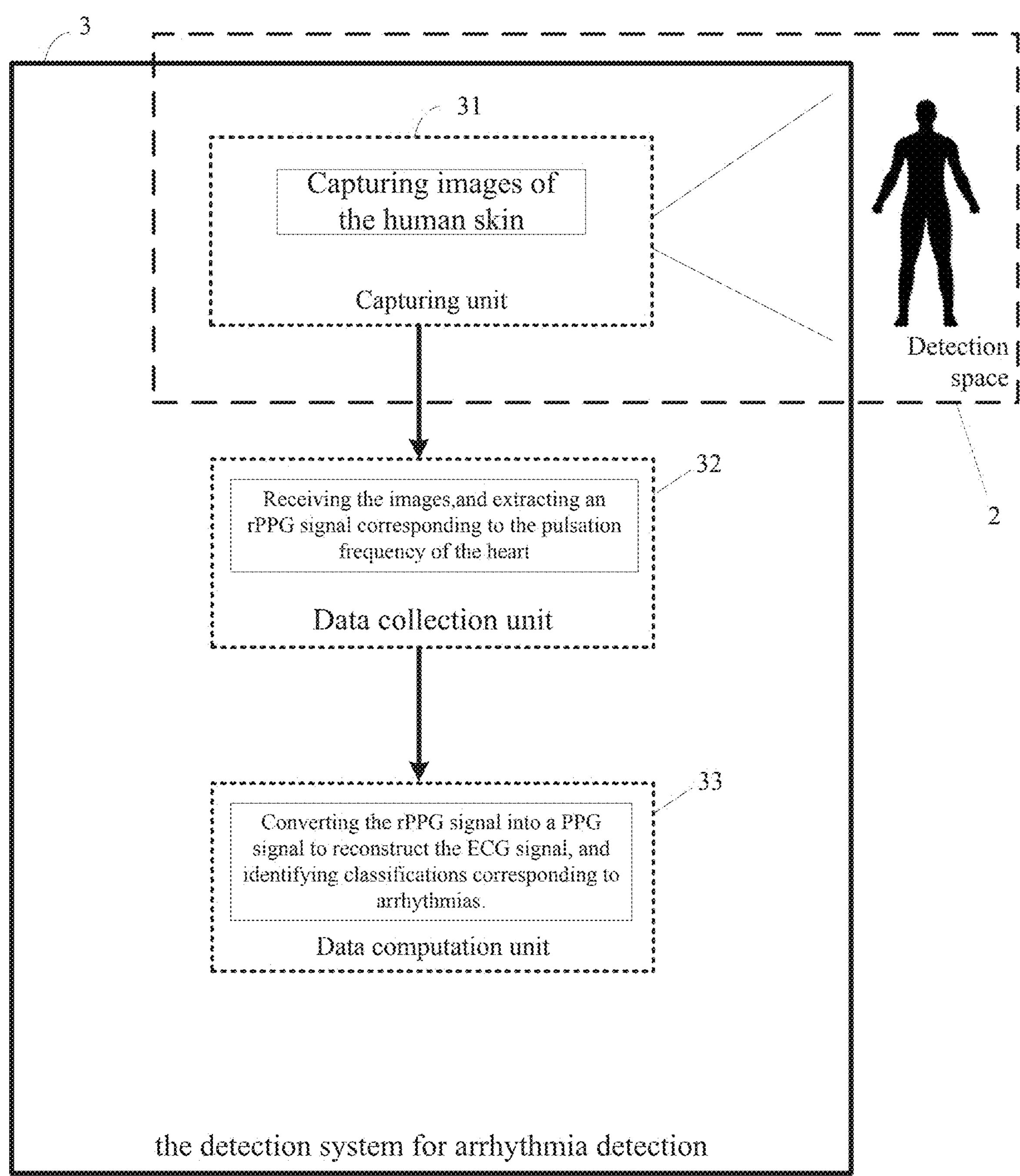
【FIG.12】

METHOD FOR RECONSTRUCTING ECG SIGNALS THROUGH IMAGING FOR ARRHYTHMIA DETECTION AND ITS DETECTION SYSTEM

CROSS-REFERENCE TO RELATED APPLICATIONS

This application claims the priority of Republic of China Patent Application No. 113108210 filed on Mar. 6, 2024, in the State Intellectual Property Office of the R.O.C., the disclosure of which is incorporated herein by reference.

BACKGROUND OF THE INVENTION

Field of the Invention

The present invention relates to a method for reconstructing ECG signals through imaging for arrhythmia detection and its detection system. More specifically, it refers to a method for reconstructing ECG signals through image detection to achieve heart rhythm monitoring and arrhythmia detection, as well as its detection system.

Descriptions of the Related Art

With the increasing personal attention to health and the rapid development of 3C technology, various wearable smart devices such as wristbands and watches have been introduced to the market. These devices can clearly display a wealth of health information, wherein photoplethysmography (PPG) is used to obtain cardiac function information for blood oxygen detection to monitor blood oxygen saturation level, and analyze heart rate data which is the number of heartbeat per minute and breathing frequency.

Moreover, the prevalence of sudden death due to cardiovascular diseases has raised widespread concern about arrhythmia, the "silent killer." Arrhythmia can be caused by various factors, including heart conditions, other medical conditions, medications, severe stress, or emotions. Arrhythmia can occur suddenly or be a chronic problem. Early detection of arrhythmia in asymptomatic patients and seeking medical help is crucial. However, the heart rate data and breathing frequency measured by the aforementioned wearable smart devices are insufficient for diagnosing and detecting arrhythmia. Therefore, electrocardiogram (ECG) recording of heart rhythm signals remains the primary method for diagnosing arrhythmia.

Currently, instruments for measuring ECG signals on the market generally use contact electrodes and are quite large. Patients need to visit medical centers for testing, which cannot be done at home. Additionally, people often do not realize they have arrhythmia, until they experience heart issues. At that point, extensive time is required for heart rhythm tracking and diagnosis. The time when the heart rhythm suddenly becomes abnormal often does not coincide with the time of the doctor's diagnosis, leading to the need for prolonged hospital stays or continuous ECG monitoring devices, which consume significant manpower and medical resources. Thus, the measurement of ECG signals has a technical barrier, making it difficult to widely promote for general public heart health care.

Therefore, solving the problem of how to enable the general public or patients requiring long-term heart rhythm monitoring to receive early warnings of potentially life-threatening arrhythmias without the use of contact electrodes and while maintaining mobility in daily life is a pressing issue in the field of technology.

SUMMARY OF THE INVENTION

In view of the drawbacks of the prior art mentioned above, the present application provides a method for reconstructing ECG signals through imaging for arrhythmia detection, comprising the following steps: (1) Receiving images of human skin, where the images contain surface color variations of the skin caused by heartbeats and heart rhythms; (2) Performing noise reduction on the color variations, and based on the analysis of the color variations, extracting an rPPG (remote-PPG; rPPG) signal corresponding to the pulsation frequency of the heart; (3) Performing frequency domain analysis to identify frequency features in the rPPG signal and performing feature extraction on a PPG signal from the frequency features; (4) Performing feature extraction on the PPG signal to extract time-domain feature and frequency-domain feature and fusing the time-domain feature and the frequency-domain feature to output a reconstructed ECG signal; and (5) Interpreting the waveform features of the reconstructed ECG signal to identify classifications corresponding to arrhythmia based on the waveform features.

Preferably, the method for reconstructing ECG signals through imaging for arrhythmia detection said above, further comprises, before performing the aforementioned step (4): a process of establishing a customized training model, which comprises the following steps: (3-1) Receiving an actual ECG signal detected by an instrument and an actual PPG signal detected by a device from a user; (3-2) Respectively extracting the peaks of the actual ECG signal and the actual PPG signal to align the actual ECG signal and the actual PPG signal, thereby eliminating the time delay between the actual ECG signal and the actual PPG signal; and (3-3) Performing time segmentation to divide the aligned actual ECG signal and the actual PPG signal into multiple segments to be used as training data for the customized training model.

Preferably, the method for reconstructing ECG signals through imaging for arrhythmia detection said above, wherein in the aforementioned step (3-3), after completing time segmentation, the following processing steps are included for the segmented actual ECG signal and the actual PPG signal: (3-3-1) Respectively comparing segments of the actual ECG signal and the actual PPG signal detected during the same period to obtain the difference between the actual ECG signal and the actual PPG signal, which serves as a customized weight for the customized training model.

Preferably, the method for reconstructing ECG signals through imaging for arrhythmia detection said above, in the aforementioned step (4), during the process of feature fusion, the reconstructed ECG signal is calibrated based on the customized weight.

Preferably, the method for reconstructing ECG signals through imaging for arrhythmia detection said above, wherein the corrected reconstructed ECG signal is compared with the actual ECG signal, and if there is a difference between the two signals, the process of the customized training model is repeated to adjust the customized weight, and the adjusted weight is then used to correct the reconstructed ECG signal during the feature fusion in step (4), thereby making the reconstructed ECG signal closer to the actual ECG signal.

Furthermore, a detection system applying the method for reconstructing ECG signals through imaging for arrhythmia detection said above, comprising: a capturing unit, which is installed in a detection space to capture images of the human skin in the detection space, for processing in step (1); a data collection unit, electrically connected to the capturing unit, for processing in step (2); and a data computation unit, electrically connected to the data collection unit, for processing in steps (3), (4), and (5).

Preferably, the detection system for arrhythmia detection said above, wherein the detection space is located in an office area, medical area, home area, public area, or a vehicle, and the data collection unit and the data computation unit can be installed in the detection space or in a location different from the one where the capturing unit is installed.

Preferably, the detection system for arrhythmia detection said above, wherein the capturing unit, data collection unit, and data computation unit are integrated into a smart device; wherein the smart device can be a camera, wearable patch, portable device, wristband, mobile phone, or computer.

Preferably, the detection system for arrhythmia detection said above, wherein the data collection unit further comprises a first interface and a second interface, the first interface being used to receive an actual ECG signal detected by an instrument from the user, and the second interface being used to receive an actual PPG signal detected by a device from the user, and the data computation unit processes the actual ECG signal and the actual PPG signal to establish a customized training model, wherein the data computation unit extracts the peaks of the actual ECG signal and the actual PPG signal, aligning the actual ECG signal and the actual PPG signal to eliminate time delay of the actual ECG signal and the actual PPG signal, then performs time segmentation to divide the aligned actual ECG signal and the actual PPG signal into multiple segments to be used as training data for the customized training model.

Additionally, the aforementioned method for reconstructing ECG signals through images for arrhythmia detection can also be applied to another detection system for arrhythmia detection, and the detection system comprises a data computation unit for performing the processes described in steps (1), (2), (3), (4), and (5) of the aforementioned method for reconstructing ECG signals through images for arrhythmia detection.

Preferably, the detection system for arrhythmia detection said above, wherein the data computation unit comprises a first interface and a second interface, the first interface being used to receive an actual ECG signal detected by an instrument from the user, and the second interface being used to receive an actual PPG signal detected by a device from the user, and the data computation unit processes the actual ECG signal and the actual PPG signal to establish a customized training model, wherein the data computation unit extracts the peaks of the actual ECG signal and the actual PPG signal, aligning the actual ECG signal and the actual PPG signal to eliminate time delay of the actual ECG signal and the actual PPG signal, then performs time segmentation to divide the aligned signals into multiple segments for use as training data in the customized training model.

In summary, the method for reconstructing ECG signals through images for arrhythmia detection and its detection system provided by the present invention offer a more comfortable and convenient alternative compared to traditional contact-based heart rate measurement methods using patches. This makes it easier to popularize among the general public and various settings. The invention focuses on utilizing artificial intelligence to analyze the features of PPG signals for ECG signal reconstruction, combined with the technology of image detection of remote PPG signals (rPPG), creating a method for reconstructing ECG signals through imaging for arrhythmia detection. Users can monitor their heart rate and heart rhythm through images while moving freely within a specific space. This method enables the general public or patients requiring long-term heart rate and heart rhythm monitoring to be alerted to their heart health before their body signals any warning signs. Therefore, by employing the present invention's method for reconstructing ECG signals through images for arrhythmia detection and its detection system, users can detect cardiovascular diseases early and achieve timely treatment.

BRIEF DESCRIPTION OF THE DRAWINGS

The above and other aspects, features and other advantages of the present invention will be more clearly understood from the following detailed description taken in conjunction with the accompanying drawings, in which:

FIG. 1 shows the processing flowchart of the method for reconstructing ECG signals through images for arrhythmia detection according to the present invention.

FIG. 2 illustrates the steps for processing rPPG signals in the method for reconstructing ECG signals through images for arrhythmia detection according to the present invention.

FIG. 3 shows the steps for converting rPPG signals into PPG signals in the method for reconstructing ECG signals through images for arrhythmia detection according to the present invention.

FIG. 4 presents the steps for reconstructing ECG signals using PPG signals in the method for reconstructing ECG signals through images for arrhythmia detection according to the present invention.

FIG. 5 provides a more detailed explanation of the steps for reconstructing ECG signals using PPG signals, as shown in FIG. 4.

FIG. 6 illustrates the processing content of the BiLSTM shown in FIG. 5.

FIG. 7 displays the processing content of the LSTM shown in FIG. 6.

FIG. 8 presents an example application of the method for reconstructing ECG signals through images for arrhythmia detection according to the present invention.

FIG. 9 describes the processing flowchart of another embodiment of the method for reconstructing ECG signals through images for arrhythmia detection according to the present invention.

FIG. 10 illustrates the processing flow for establishing a customized training model, as shown in FIG. 9.

FIG. 11 explains an example of how the correction of reconstructed ECG signals after applying the customized training model shown in FIG. 10 can yield results closer to the actual ECG signals measured by an electrocardiogram device.

FIG. 12 provides a schematic diagram of the basic structure of a detection system that can apply the method for reconstructing ECG signals through images for arrhythmia detection according to the present invention.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art.

In recent years, due to the ravages of the COVID-19 pandemic, telemedicine and non-contact physiological signal measurement methods have been introduced rapidly, among which the technology based on remote photoplethysmography (rPPG) signal detection through images has grown remarkably fast. This is a non-contact method for measuring blood oxygen signals. The present invention utilizes this non-contact blood oxygen measurement technology to collect users' heartbeat data as a data source for reconstructing ECG signals. With the rPPG signal technology, users can move freely within a detection space, which can be set up in areas such as offices, medical areas, home areas, public areas, or transportation vehicles. Particularly, through this invention, it is possible to detect users who may be prone to overwork in office areas, medical areas, or transportation vehicles early on, allowing medical personnel to assess and develop appropriate treatment plans for potential arrhythmias. Therefore, this invention allows users to monitor their heart rhythm through images in a specific area while being able to move freely. Users can not only know the number of heartbeats per minute but also monitor their heart rhythm to understand their heart's health status.

Please refer to FIG. 1, which illustrates the flowchart of the steps for detecting arrhythmias using the method for reconstructing ECG signals through imaging according to the present invention. As shown in the figure, the first step S10, involves capturing an image of the human skin through a capturing device, which contains color changes on the skin surface caused by heartbeats and heart rhythms. This is followed by step S11.

In step S11, the color changes undergo noise reduction processing. Based on the analysis of these color changes, an rPPG signal corresponding to the heart rate is extracted. This is followed by step S12.

It should be noted that the pulse is a pressure wave generated by the heartbeat that propagates through the blood vessels and can be sensed on the body surface, typically allowing for single-point measurement of heart rate. The goal of step S11 is to extract precise heart rate information from the three-dimensional images captured by the capturing device while minimizing the influence of environmental factors, lighting, motion, and other interferences. Therefore, for rPPG signal processing, as detailed in FIG. 2, noise reduction is first performed to remove interference and noise from the color changes, thereby enhancing the accuracy and reliability of heart rate information. This is because the images of human skin captured by the capturing device may be affected by various interferences, such as variations in ambient light, motion blur caused by human movement, and noise from the capturing device itself. Filters can be applied to eliminate high-frequency noise and other unwanted signal components. Common filters include low-pass filters, high-pass filters, band-pass filters, and band-stop filters. Proper filtering helps retain the pulse and heart rhythm components in the signal.

After noise reduction, target masking and segmentation are performed. In the processing of image data, target masking is a binary mask used to indicate specific regions or targets in an image. In rPPG signal processing, target masking is employed to mark skin areas, specifically extracting regions of interest such as the face, cheeks, forehead, fingers, palms, and back of the hands, where color changes caused by heartbeats and heart rhythms are more easily observable. This allows for a more focused analysis of changes related to heartbeats and heart rhythms. This can be accomplished by first preprocessing the image, using skin detection algorithms to generate a skin mask, and then applying this mask to the original image. Segmentation techniques can be used to distinguish different physiological structures or regions, such as the face, cheeks, forehead, fingers, palms, and back of the hands, where microvascular observations can be made. This aids in more precise analysis of specific areas, enhancing the extraction of heartbeat information.

After extracting the regions of interest from the images of human skin, since these areas readily display color changes caused by heartbeats and heart rhythms, information related to heartbeats and heart rhythms can be extracted by calculating pixel changes. This is based on the principle that color changes in the skin correlate with heartbeats and heart rhythms; when the heart beats, blood flow through the skin can cause slight changes in skin color. The capturing device can capture these subtle changes, and by calculating the variations in each pixel of the image, information related to heartbeats and heart rhythms can be extracted. When processing rPPG signals, this method is typically referred to as video photoplethysmogram (vPPG). By analyzing the image sequences of skin regions captured by the capturing device, changes in skin color can be calculated, thus extracting information related to heartbeats and heart rhythms.

Next, please return to FIG. 1. In step S12, frequency domain analysis is performed to identify the frequency features within the rPPG signal, and feature extraction is conducted to obtain a PPG signal. The processing of converting the rPPG signal to the PPG signal is detailed in FIG. 3, where noise reduction is performed on the rPPG signal output from step S11 to enhance the quality of the rPPG signal. Compared to the noise reduction in FIG. 2, this noise reduction aims to improve the purity of the rPPG signal, ensuring that the subsequent converted PPG signal is more reliable and stable. Signal processing is conducted to enhance the quality of the rPPG signal, including extracting information related to heartbeat-related features to ensure that subsequent processing steps can better capture and utilize the PPG signal related to heartbeats and heart rhythm features.

In step S13, feature extraction is performed on the PPG signal to extract the time domain feature and the frequency domain feature, and the time domain feature and the frequency domain feature are fused to output a reconstructed ECG signal. The processing of reconstructing the ECG signal from the PPG signal is detailed in FIG. 4, where noise reduction is applied to the PPG signal output from step S12 to enhance the quality of the PPG signal, aiding in ensuring the reliability and stability of the subsequent reconstructed ECG signal.

In the process of reconstructing the ECG signal from the PPG signal, steps such as pulse transit time removing and temporal segmentation are performed to improve signal quality and extract specific features. The pulse transit time in the PPG signal refers to the time it takes for the optical pulse to reach different depths of the skin, which is usually caused by differences in the speed of light propagation in different tissue layers. The purpose of removing pulse transit time is to enhance the accuracy of the ECG signal and reduce phase differences caused by different depths. Signal processing techniques for pulse transit time removal, such as cross-correlation or phase correction, can be employed to correct the time delays in the PPG signal, ensuring that the specific features of the PPG signal (e.g., pulse wave peak) remain synchronized with features in the ECG signal.

The PPG signal typically contains information from multiple cardiac cycles; however, this information may vary across different time segments within the signal. Therefore, through temporal segmentation, we can ensure that specific parts of the ECG signal correspond with the respective parts in the PPG signal, allowing for the accurate extraction of heartbeat and rhythm information. Temporal segmentation can be achieved by dividing the PPG signal into fixed time windows and then determining how each time window's PPG signal corresponds with specific cardiac cycles in the ECG signal. This may involve further processing for signal alignment and correction.

The purpose of the above processing steps is to ensure that specific features in the PPG signal remain synchronized with the corresponding features in the ECG signal, allowing for effective extraction of heartbeat and heart rhythm information and cardiac state diagnosis. These methods combine signal processing and temporal analysis techniques to maximize the accuracy of the model.

More specifically, in the process of reconstructing the ECG signal from the PPG signal, this invention employs a neural network model for hierarchical feature extraction and feature fusion. By utilizing hierarchical feature extraction and feature fusion techniques, multiple segmented PPG sequence data are extracted and combined, as shown in FIG. 5, which provides more detailed processing steps in the processing shown in FIG. 4. In the neural network, different hierarchical structures and activation functions can be used to perform feature extraction, as illustrated in the hierarchical feature extraction process A1 in FIG. 5. This invention employs bidirectional long short-term memory (BiLSTM) to capture backward information in the segmented PPG sequence data. The BiLSTM structure has both forward and backward directions; this structure is designed to consider not only past information (forward) but also future information (backward) when processing sequential data, thereby more comprehensively capturing contextual information within the sequence. Therefore, by increasing the complexity of feature decomposition operations, the accuracy of signal reconstruction can be improved. In this embodiment, the features A shown in FIG. 4 represent the results output by the first layer of BiLSTM, while features B represent the results output by the second layer of BiLSTM, and so on. This concept distributes the feature learning process across different layers (different operations), enhancing the efficiency and accuracy of signal reconstruction. In the BiLSTM, the input at each time point in the sequence data is processed by two directional LSTM units. The forward LSTM processes from the start of the sequence, while the backward LSTM processes from the end of the sequence. This allows the neural network to better understand the information at each time point within the sequence and consider the entire context of the sequence more comprehensively during learning. The BiLSTM aids in a more comprehensive understanding of sequential data. This step emphasizes extracting specific signals associated with cardiac activity from multiple segmented PPG sequence data, such as wave peaks and wave patterns, which are valuable for assessing physiological parameters like heart rate and rhythm. Here, the features are typically measurements with clear physical significance in the time or frequency domain. In this embodiment, the attention backward layer, as shown in FIG. 5, performs feature fusion ($F_1$, $F_2$, $F_3$, . . . , $F_i$) processing through dense connections, as depicted in FIG. 5. The feature fusion processing A2 involves combining time-domain and frequency-domain features, thereby outputting a reconstructed ECG signal.

$$y = \sum_{i=1}^{n} w_i h_i(x), \qquad \text{equation (1)}$$

$$f_n' = F(x_n) = \sum_{i=2}^{n} f_{i-1} \qquad \text{equation (2)}$$

Wherein x represents the input PPG signal, and y represents the output reconstructed ECG signal.

Please refer to FIG. 6 for the input of each BiLSTM layer. Each input of the BiLSTM layer is:

$$x_n = \sum_{i=2}^{n} y_{i-1} \qquad \text{equation (3)}$$

The signals $f_1$~$f_i$ shown in FIG. 5 are the outputs ($y_n$) of each BiLSTM layer; the final layer of the fully connected layer (Fc) is:

$$y_i = W_i x_i + b_i, \qquad \text{equation (4)}$$

The calculation performed by the neurons ($F_1$~$F_i$) in the neural network is:

$$f_n' = F(x_n) = \sum_{i=2}^{n} f_{i-1} \qquad \text{same as equation (2)}$$

The coefficients in the above calculation (e.g., W, b, etc.) serve as the weights of the transformation function in the conversion between input x and output y. These coefficients are key indicators for each layer of the neural network to identify relatively important features. In the neural network, an activation function is applied to the output of the neurons to introduce non-linearity. The activation function is crucial for the training and learning of the neural network, enabling it to learn more complex patterns and features. In this invention, an example of the activation function used is the tanh, but other activation functions can also be utilized for computation. The calculation of this BiLSTM example is as follows:

$$y_{t,bilstm} = \tanh(y_{t,forward} + y_{t,backward}), \qquad \text{equation (5)}$$

Additionally, please refer to FIG. 7, which illustrates the corresponding computations and operations performed in the LSTM neural network as shown in FIG. 6. LSTM (Long Short-Term Memory) adds memory units to the recurrent neural network (RNN) architecture, enabling it to process long-term sequence data. The LSTM model consists of the current input $X_t$, the memory state $C_t$, the temporary memory state $\check{C}_t$, the hidden layer state $h_t$, the forget gate $f_t$, the input gate $i_t$, and the output gate $o_t$. The LSTM's calculation process can be summarized as transmitting useful information for subsequent time-step calculations by forgetting information in the memory state and remembering new information and unnecessary information is discarded. At each time step, the hidden layer state $h_t$ is output. The forgetting, remembering, and outputting processes are controlled by the forget gate $f_t$, input gate $i_t$, and output gate $o_t$, which are calculated based on the hidden layer state $h_{t-1}$ from the previous time step and the current input $X_t$. The processing comprises:

$$y_t = h_t, \quad \text{equation (6)}$$

$$h_t = o_t \tanh(c_t) \quad \text{equation (7)}$$

$$c_t = f_t c_{t-1} + i_t \tilde{c}_t, \quad \text{equation (8)}$$

$$\tilde{c}_t = \tanh(Wh_{t-1} + Ux_t + b), \quad \text{equation (9)}$$

$$o_t = \sigma(W_o h_{t-1} + U_o x_t + b_o), \quad \text{equation (10)}$$

$$f_t = \sigma(W_f h_{t-1} + U_f x_t + b_f), \quad \text{equation (11)}$$

$$i_t = \sigma(W_i h_{t-1} + U_i x_t + b_i), \quad \text{equation (12)}$$

$$y_{t\text{-}lstm} = o_t \cdot \tanh(f_t \cdot c_{t-1} + i_t \cdot \tanh(Wh_{t-1} + Ux_t + b)), \quad \text{equation (13)}$$

Next, please return to FIG. 1. In step S14 of this process, the reconstructed ECG signal output from step S13 is analyzed. Based on the waveform characteristics of the reconstructed ECG signal, classifications corresponding to arrhythmias are detected, as shown in FIG. 8. This demonstrates an application example of the method for identifying arrhythmias using the image reconstruction of ECG signals according to the present invention. The present invention compares the waveform characteristics B1 of the reconstructed ECG signal with multiple pre-stored ECG waveform feature parameters B2 for classification. These feature parameters B2 include, for example: normal sinus rhythm, atrial fibrillation, premature ventricular contraction, atrial premature complexes, or ventricular tachycardia.

Therefore, the method for identifying arrhythmias through image reconstruction of ECG signals utilizes a non-contact measurement technique to capture data related to heartbeats from observable areas of the skin microvasculature (such as the face, cheeks, forehead, fingers, palms, and backs of the hands). This is followed by the detection of the rPPG signal using artificial intelligence algorithms. Next, to equate the quality of the rPPG signal to that of the PPG signal, a conversion between the rPPG and PPG signals is performed. The features of the reconstructed ECG signal are learned from the PPG signal to identify and distinguish normal rhythms, atrial fibrillation (AF), and non-atrial fibrillation arrhythmias based on the heart rhythm signal obtained from the reconstructed ECG signal. This allows users to monitor their heart rhythm in a non-contact manner according to their environment, without the need to wear measurement devices, and to assess the risk of arrhythmias, achieving the goals of regular monitoring and early detection and treatment.

Furthermore, please refer to FIG. 9, which illustrates another embodiment of the method for identifying arrhythmias using image reconstruction of ECG signals. The processing steps S11', S12', S13', and S14' shown in FIG. 9 correspond to the processing of steps S11, S12, S13, and S14 in FIG. 1. The difference between FIG. 9 and FIG. 1 is that it also comprises step S15, which involves establishing a customized training model. The establishment process of this customized training model is illustrated in FIG. 10. First, preprocessing is performed on an actual ECG signal E1 and an actual PPG signal P1, where the actual ECG signal E1 is obtained through medical instruments that measure electrocardiograms, and the actual PPG signal P1 is obtained through contact devices that can measure PPG signals (such as fitness bands or smartwatches). The actual ECG signal E1 and the actual PPG signal P1 are then used to fine-tune the reconstruction of the ECG signal in step S13 of FIG. 1 or step S13' of FIG. 9. Preprocessing comprises extracting the peak values of both the actual ECG signal E1 and the actual PPG signal P1 to align them, thus eliminating the time delay between the two signals. Following this, a time-segmenting process is conducted to divide the aligned actual ECG signal E1 and actual PPG signal P1 into multiple segments for use as training data in the customized training model.

Upon completion of the above time-segmenting process, the actual ECG signals and actual PPG signals from each segmented portion detected simultaneously are compared to obtain the differences between the two signals, which serves as a customized weight for the training model. Therefore, the present invention provides functionality for comparing the reconstructed ECG with the actual ECG, realizing a learning training process to enhance the accuracy of the reconstructed ECG. When it is confirmed that the accuracy of the reconstructed ECG is insufficient compared to the actual ECG, the customized weight output from FIG. 5 can be fed back into the neural network shown in FIG. 4 to calibrate the network for outputting the reconstructed ECG signal that combines temporal and frequency domain features.

As can be seen, in order to make the reconstructed ECG signal more accurate and closer to the actual ECG signal, the present invention performs calibration processing on the reconstructed ECG signal output from feature fusion. Furthermore, the calibrated reconstructed ECG signal can again be compared with the actual ECG signal. If the two signals still exhibit differences, indicating insufficient accuracy, the customized training model process can be repeated, further adjusting the customized weights. Thus, during the subsequent processing of the reconstructed ECG signal, the adjusted customized weights are used for calibration during the feature fusion step. As shown in FIG. 11, this explains how the present invention utilizes customized training to calibrate the reconstructed ECG signal to be closer to the actual ECG signal measured by electrocardiogram acquisition devices. As illustrated, the reconstructed ECG signal D1 before calibration becomes the calibrated reconstructed ECG signal D2 after the aforementioned customized training, which is more aligned with the actual ECG signal E1.

Furthermore, the method for identifying arrhythmias through image reconstruction of ECG signals can be applied to a detection system 3 for identifying arrhythmias, as shown in FIG. 12. This detection system 3 comprises: a capturing unit 31, a data collection unit 32, and a data computation unit 33. The capturing unit 31 is set up in a detection space 2, which can be located in office areas, medical areas, home areas, public areas, or on transportation vehicles to capture images of the skin of individuals located in that detection space 2. In this embodiment, the data collection unit 32 and the data computation unit 33 are positioned separately from the capturing unit 31. However, the data collection unit 32 and the data computation unit 33 can also be set up together in the detection space 2 or separately. For example, the capturing unit 31, data collection unit 32, and data computation unit 33 can be integrated into a smart device, which can be a camera, wearable patch, portable device, wristband, smartphone, or computer. Therefore, the configuration or arrangement of the capturing unit 31, data collection unit 32, and data computation unit 33 may vary depending on the implementation type. The data collection unit 32 is electrically connected to the capturing unit 31, and both are used to perform the processing steps S10 and S11 shown in FIG. 1. The data computation unit 33 is electrically connected to the data collection unit 32, which performs the processing steps S12, S13, and S14 as shown in FIG. 1.

In this embodiment, the data collection unit 32 also has a first interface and a second interface, which are used to implement the customized training process shown in FIG. 10. Specifically, the first interface receives input from the actual ECG signal E1, and the second interface receives input from the actual PPG signal P1. The data collection unit 32 processes the received actual ECG signal E1 and actual PPG signal P1 according to the preprocessing and fine-tuning processes shown in FIG. 10 to obtain a customized weight for subsequent feature fusion steps, allowing calibration of the reconstructed ECG signal to make it closer to the actual ECG signal.

Additionally, another embodiment of the detection system for identifying arrhythmias may omit the capturing unit 31 and a data collection unit 32. In this case, the detection system comprises only the data computation unit 33, which is electrically connected to an imaging device used to capture images of the skin of individuals in the detection space. The data computation unit 33 performs the steps S10, S11, S12, S13, and S14 as shown in FIG. 1. Regarding the establishment of the customized training model, the data computation unit also has the first interface and the second interface to receive inputs from the actual ECG signal E1 and the actual PPG signal P1, allowing the data collection unit 32 to perform preprocessing and fine-tuning as shown in FIG. 10.

Therefore, the method for identifying arrhythmias through image reconstruction of ECG signals and its detection system addresses the issues of current ECG measurements requiring numerous electrode patches to be attached to the body, large equipment sizes, and complex procedural steps. At the same time, they enable effective monitoring of specific locations, particularly providing more effective health management for individuals living alone or workers prone to overexertion, thus helping to prevent sudden cardiac death due to cardiovascular diseases.

The examples above are only illustrative to explain principles and effects of the invention, but not to limit the invention. It will be apparent to those skilled in the art that modifications and variations can be made without departing from the spirit and scope of the invention. Therefore, the protection range of the rights of the invention should be as defined by the appended claims.

What is claimed is:

1. A method for reconstructing ECG signals through imaging for arrhythmia detection, comprising the following steps:

(1) Receiving images of human skin in microvascular observable areas, where the images contain surface color variations of the human skin caused by heartbeats and heart rhythms;

(2) Performing noise reduction on the surface color variations, and based on an analysis of the color variations, extracting an rPPG signal corresponding to a pulsation frequency of a heart, wherein the pulsation frequency is correlated with cardiac behaviors including the heartbeats and heart rhythms;

(3) Performing frequency domain analysis to identify frequency features in the rPPG signal and performing feature extraction on a PPG signal based on the identified frequency features, wherein the PPG signal is the rPPG signal that has been subjected to a standardization or preprocessing procedure;

(4) Performing the feature extraction on the PPG signal to extract time-domain feature and frequency-domain feature and fusing the time-domain feature and the frequency-domain feature through a hierarchical feature fusion technique to output a reconstructed ECG signal, wherein the reconstructed ECG signal refers to an analog signal that contains core physiological information of ECG and is generated by simulating ECG physiological information based on the PPG signal; and (5) Interpreting waveform features of the reconstructed ECG signal to identify classifications corresponding to arrhythmia based on the waveform features.

2. The method for reconstructing ECG signals through imaging for arrhythmia detection as described in claim 1, further comprises, before performing the aforementioned step (4): a process of establishing a customized training model, which comprises the following steps:

(3-1) Receiving an actual ECG signal detected by an instrument and an actual PPG signal detected by a device from a user;

(3-2) Respectively extracting the peaks of the actual ECG signal and the actual PPG signal to align the actual ECG signal and the actual PPG signal, thereby eliminating the time delay between the actual ECG signal and the actual PPG signal; and (3-3) Performing time segmentation to divide the aligned actual ECG signal and the actual PPG signal into multiple segments to be used as training data for the customized training model.

3. The method for reconstructing ECG signals through imaging for arrhythmia detection as described in claim 2, wherein in the aforementioned step (3-3), after completing time segmentation, the following processing steps are included for the segmented actual ECG signal and the actual PPG signal:

(3-3-1) Respectively comparing segments of the actual ECG signal and the actual PPG signal detected during the same period to obtain the difference between the actual ECG signal and the actual PPG signal, which serves as a customized weight for the customized training model.

4. The method for reconstructing ECG signals through imaging for arrhythmia detection as described in claim 3, wherein in the aforementioned step (4), when performing feature fusion of the time-domain feature and frequency-domain feature to output the reconstructed ECG signal, the following step is included:

(4-1) Correcting the reconstructed ECG signal using the customized weight.

5. The method for reconstructing ECG signals through imaging for arrhythmia detection as described in claim 4, wherein the corrected reconstructed ECG signal is compared with the actual ECG signal, and if there is a difference between the two signals, the process of the customized training model is repeated to adjust the customized weight, and the adjusted weight is then used to correct the reconstructed ECG signal during the feature fusion in step (4), thereby making the reconstructed ECG signal closer to the actual ECG signal.

6. A detection system applying the method for reconstructing ECG signals through imaging for arrhythmia detection as described in claim 1, comprising:

a capturing unit, which is installed in a detection space to capture images of the human skin in the detection space, for processing in step (1);

a data collection unit, electrically connected to the capturing unit, for processing in step (2); and a data computation unit, electrically connected to the data collection unit, for processing in steps (3), (4), and (5).

7. The detection system as described in claim 6, wherein the detection space is located in an office area, medical area, home area, public area, or a vehicle, and the data collection unit and the data computation unit can be installed in the detection space or in a location different from the one where the capturing unit is installed.

8. The detection system as described in claim 6, wherein the capturing unit, data collection unit, and data computation unit are integrated into a smart device.

9. The detection system as described in claim 8, wherein the smart device can be a camera, wearable patch, portable device, wristband, mobile phone, or computer.

10. The detection system as described in claim 6, wherein the data collection unit further comprises a first interface and a second interface, the first interface being used to receive an actual ECG signal detected by an instrument from the user, and the second interface being used to receive an actual PPG signal detected by a device from the user, and the data computation unit processes the actual ECG signal and the actual PPG signal to establish a customized training model, wherein the data computation unit extracts the peaks of the actual ECG signal and the actual PPG signal, aligning the actual ECG signal and the actual PPG signal to eliminate time delay of the actual ECG signal and the actual PPG signal, then performs time segmentation to divide the aligned actual ECG signal and the actual PPG signal into multiple segments to be used as training data for the customized training model.

11. The detection system as described in claim 10, wherein after completing time segmentation, the data computation unit compares the segments of the actual ECG signal and the actual PPG signal detected in the same period to obtain the difference between the actual ECG signal and the actual PPG signal, which serves as a customized weight for the customized training model.

12. The detection system as described in claim 11, wherein in step (4), the data computation unit performs feature fusion of the time-domain feature and the frequency-domain feature to output the reconstructed ECG signal, and uses the customized weight to correct the reconstructed ECG signal.

13. The detection system as described in claim 12, wherein the data computation unit compares the corrected reconstructed ECG signal with the actual ECG signal, and if there is a difference between the two signals, the process of the customized training model is repeated to adjust the customized weight, and the adjusted weight is then used to correct the reconstructed ECG signal during the feature fusion in step (4), thereby making the reconstructed ECG signal closer to the actual ECG signal.

14. A detection system applying the method for reconstructing ECG signals through imaging for arrhythmia detection as described in claim 1, for processing images of human skin captured by a capturing unit installed in a detection space, comprising:

a data computation unit for processing the steps (1), (2), (3), (4), and (5).

15. The detection system as described in claim 14, wherein the data computation unit comprises a first interface and a second interface, the first interface being used to receive an actual ECG signal detected by an instrument from the user, and the second interface being used to receive an actual PPG signal detected by a device from the user, and the data computation unit processes the actual ECG signal and the actual PPG signal to establish a customized training model, wherein the data computation unit extracts the peaks of the actual ECG signal and the actual PPG signal, aligning the actual ECG signal and the actual PPG signal to eliminate time delay of the actual ECG signal and the actual PPG signal, then performs time segmentation to divide the aligned signals into multiple segments for use as training data in the customized training model.

16. The detection system as described in claim 15, wherein after completing time segmentation of the data computation unit, the data computation unit compares the segments of the actual ECG signal and the actual PPG signal detected in the same period to obtain the difference between the actual ECG signal and the actual PPG signal, which serves as a customized weight for the customized training model.

17. The detection system as described in claim 16, wherein in step (4), the data computation unit performs feature fusion of the time-domain feature and the frequency-domain feature to output the reconstructed ECG signal, and uses the customized weight to correct the reconstructed ECG signal.

18. The detection system as described in claim 17, wherein the data computation unit compares the corrected reconstructed ECG signal with the actual ECG signal, and if there is a difference between the two signals, the process of the customized training model is repeated to adjust the customized weight, and the adjusted weight is then used to correct the reconstructed ECG signal during the feature fusion in step (4), thereby making the reconstructed ECG signal closer to the actual ECG signal.

* * * * *